United States Patent [19]

VanVliet

[11] Patent Number: 4,726,874
[45] Date of Patent: Feb. 23, 1988

[54] WAIST ELASTIC APPLICATOR FOR DIAPER OR SIMILAR ARTICLE

[75] Inventor: Raymond A. VanVliet, Auburn, Wash.

[73] Assignee: Weyerhaeuser Company, Tacoma, Wash.

[21] Appl. No.: 32,271

[22] Filed: Mar. 31, 1987

[51] Int. Cl.[4] .................................. B32B 31/00
[52] U.S. Cl. ......................... 156/495; 156/163; 156/229; 156/497; 156/519; 156/520; 156/521; 156/560; 156/568
[58] Field of Search ............... 156/163, 164, 229, 495, 156/497, 519, 520, 521, 560, 568

[56] References Cited

U.S. PATENT DOCUMENTS

| | | | |
|---|---|---|---|
| 2,601,005 | 6/1952 | Raney | 154/80 |
| 3,520,303 | 7/1970 | Endres | 128/287 |
| 3,728,191 | 4/1973 | Wierzba et al. | 156/265 |
| 3,850,724 | 11/1974 | Lehmacher | 156/519 |
| 3,897,293 | 7/1975 | Babcock | 156/227 |
| 3,951,150 | 4/1976 | Schaar | 128/287 |
| 3,960,641 | 6/1976 | Pedersen | 156/519 |
| 4,135,343 | 1/1979 | Urban et al. | 53/435 |
| 4,205,679 | 6/1980 | Repke et al. | 128/287 |
| 4,279,686 | 7/1981 | Achelpohl et al. | 156/517 |
| 4,284,454 | 8/1981 | Joa | 156/229 |
| 4,285,747 | 8/1981 | Rega | 156/164 |
| 4,289,567 | 9/1981 | Achelpohl | 156/517 |
| 4,316,756 | 2/1982 | Wilson | 156/227 |
| 4,357,197 | 11/1982 | Wilson | 156/354 |
| 4,378,261 | 3/1983 | Burns et al. | 156/163 |
| 4,381,781 | 5/1983 | Sciaraffa et al. | 604/372 |
| 4,430,086 | 2/1984 | Repke | 604/385 |
| 4,502,904 | 3/1985 | Clark | 156/519 |
| 4,523,969 | 6/1985 | Spencer | 156/164 |
| 4,608,115 | 8/1986 | Schroth et al. | 156/164 |
| 4,617,082 | 10/1986 | Oshefsky et al. | 156/164 |
| 4,642,151 | 2/1987 | Coenen | 156/164 |

Primary Examiner—Jerome Massie

[57] ABSTRACT

The invention is an apparatus for applying a tensioned elastic ribbon or ribbons transversely of a moving web or material. It is particularly well adapted for applying elastic to the waist zones of disposable diapers moving continuously in an end-to-end assembly. The apparatus has a supporting frame with a shaft providing an axis of rotation for at least one rotatable radial arm. A polygonal head is mounted at the end of each arm. This has a number of peripheral edges with clamps or vacuum orifices for holding a tensioned strand or strands of elastic ribbon. A drive rotates the radial arms and a rotating mechanism moves the heads (360/n)° for each full rotation of the radial arms where n is equal to the number of peripheral faces on the head. An anvil acts against the head at the time of application of the tensioned elastic to the moving web. The web is passed between the head and the anvil along a path describing a chord or tangent of the circle of rotation of the radial arms.

15 Claims, 16 Drawing Figures

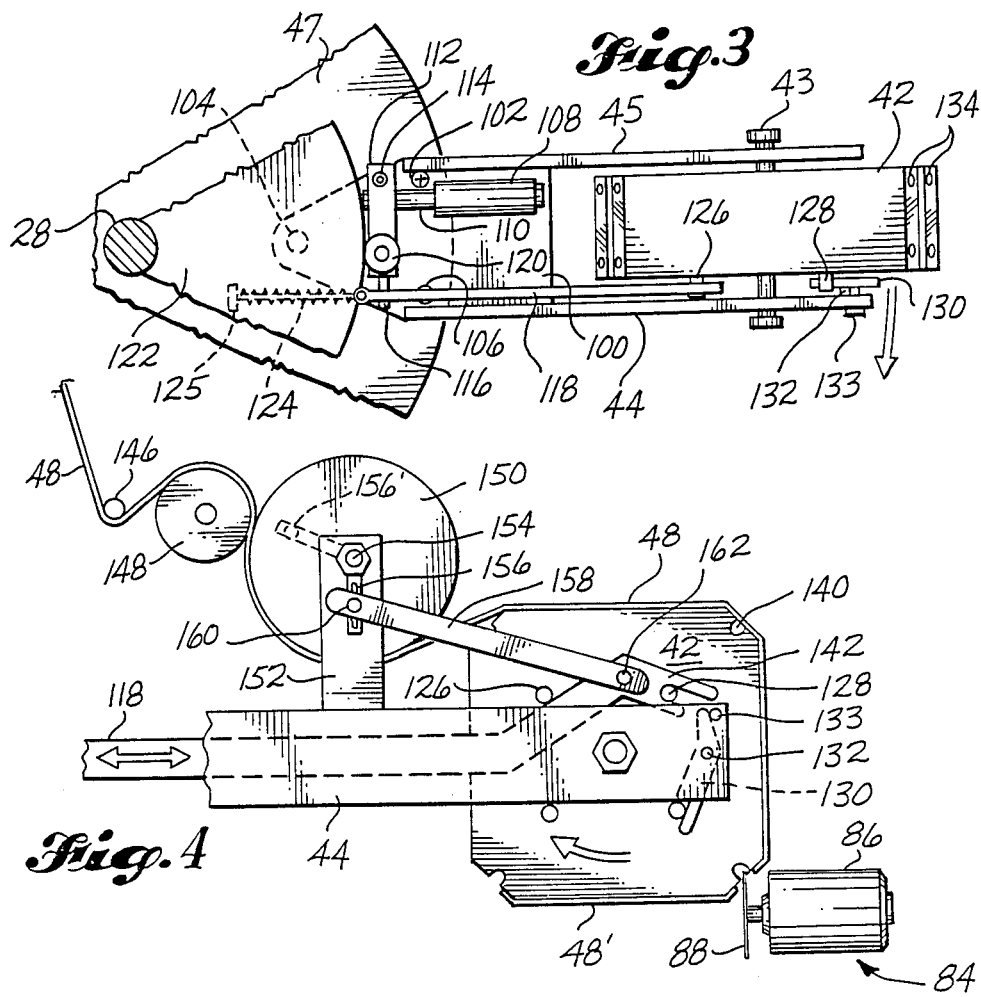
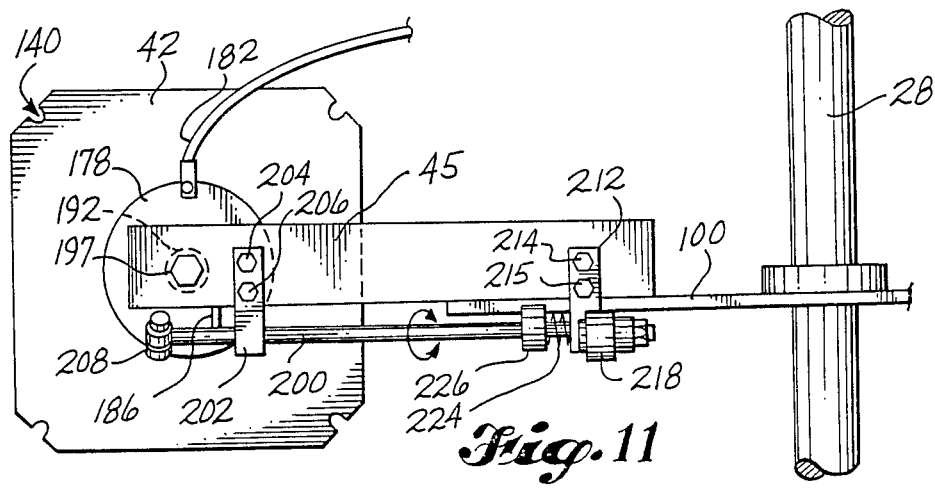

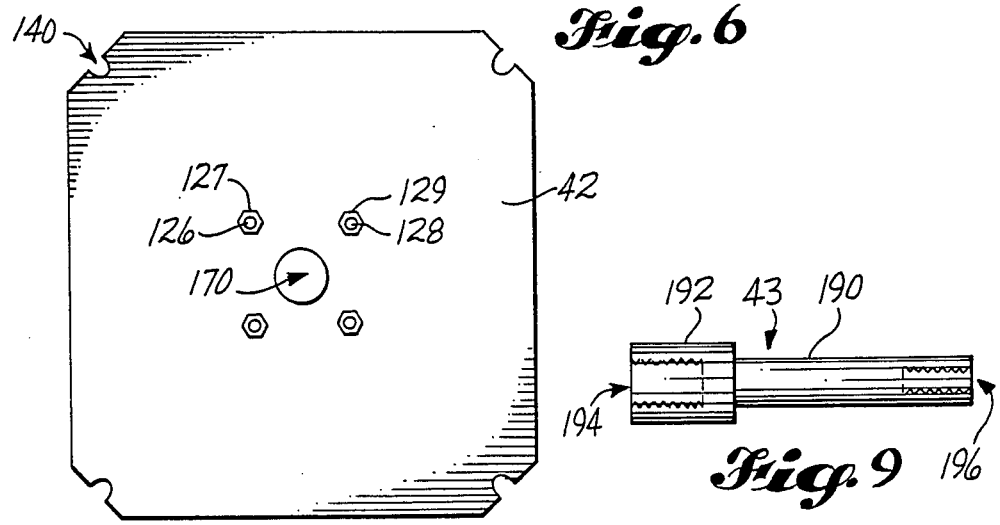
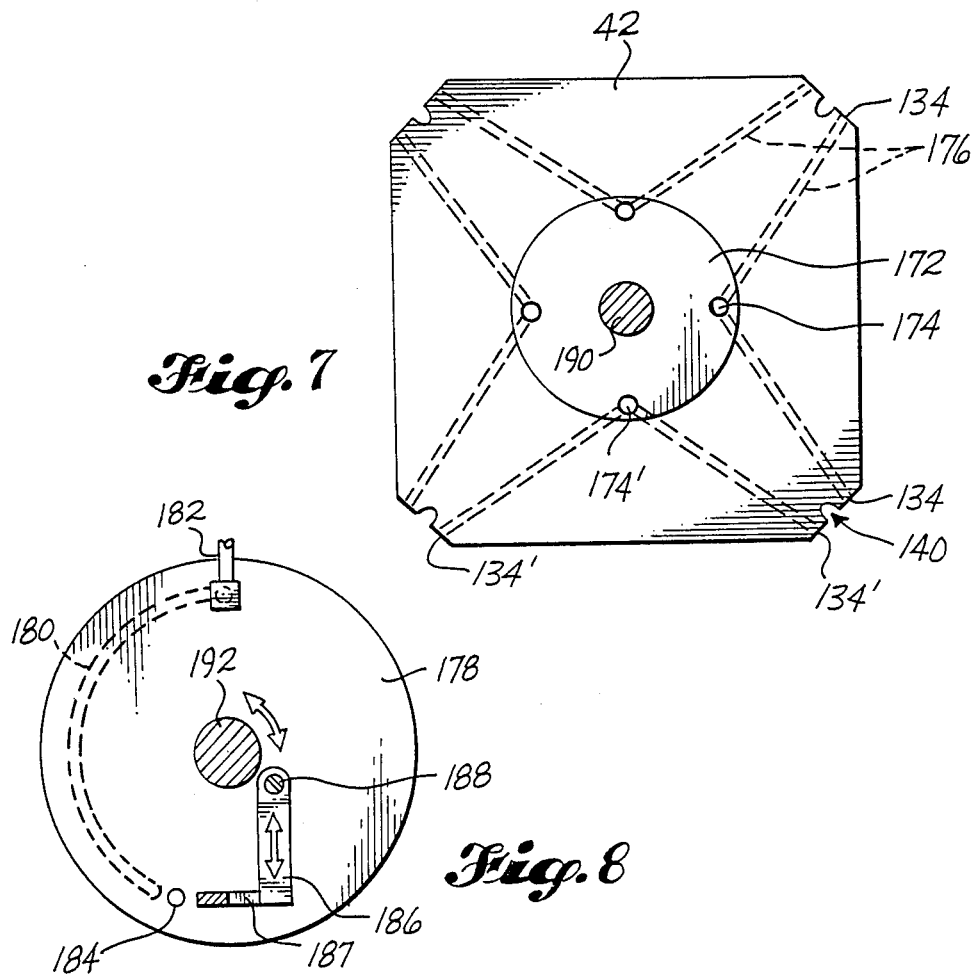

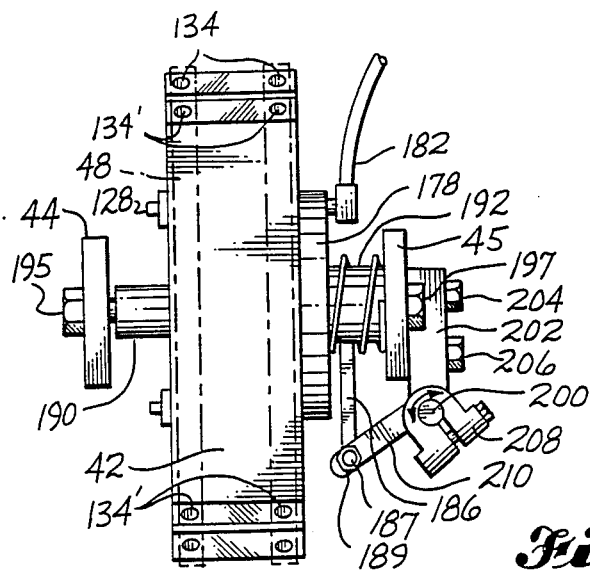
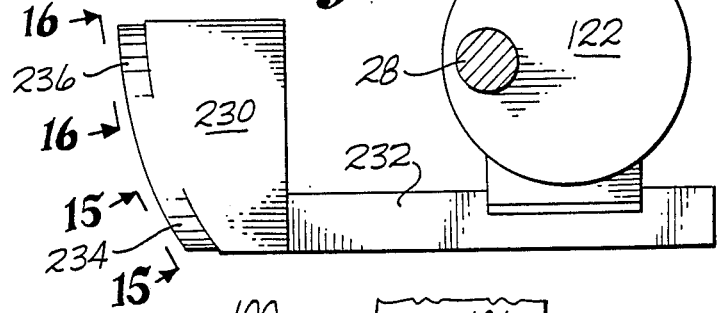
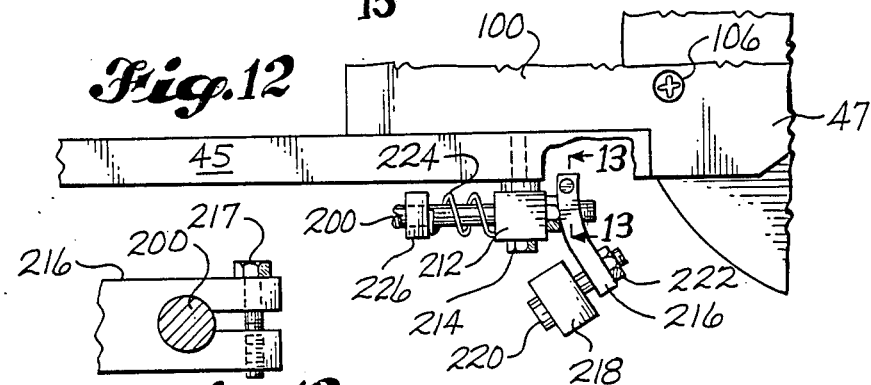
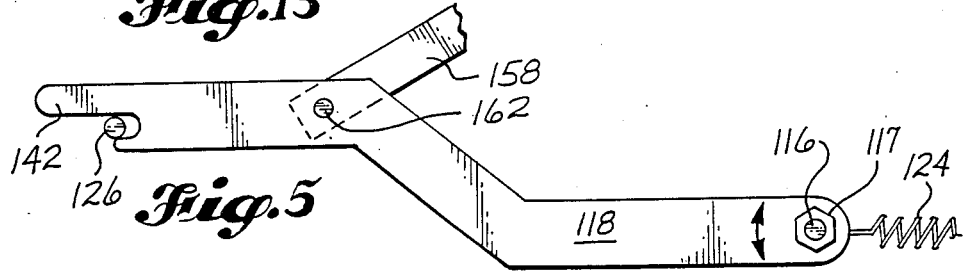

WAIST ELASTIC APPLICATOR FOR DIAPER OR SIMILAR ARTICLE

BACKGROUND OF THE INVENTION

The present invention relates to apparatus for applying a tensioned elastic member transversely to a moving web of material. More specifically, the apparatus is useful for applying waist zone elastic to a moving assembly in the manufacture of disposable diapers.

Longitudinally positioned elastic in the leg encircling zones of disposable diapers represented a major improvement in the reduction of leakage. A diaper of this type is shown generally in U.S. Pat. No. 3,860,003 to Buell. Machinery for manufacturing the above diaper is described in U.S. Pat. No. 4,081,301 to the same inventor. Subsequent to this time, other inventors in the field have placed elastic in the waist area in order to ensure a more comfortable and leak resistant fit. Examples of diapers of this type are seen in U.S. Pat. Nos. 3,951,150 to Schaar, Repke et al, 4,205,679; Sciaraffa et al, 4,381,781 and Repke et al, 4,430,086. The references just cited and intended to be exemplary and not inclusive.

Diapers are normally manufactured in a continuous end-to-end assembly. While the exact manufacturing process will vary somewhat between different manufactures, most typically preformed absorbent pads of fluffed wood pulp are laid down in a spaced-apart relationship on a continuous sheet of thin polyethylene. These are then covered with a nonwoven fabric which forms the skin contacting surface when in use. Many variations occur in this general procedure including the application of leg elastic, and adhesive attachment tabs in what will become the waist area. One could assume that the application of longitudinally oriented elastic to the moving diaper assembly would be a relatively simple operation. That this is not so is well shown by the considerably number of United States and foreign patents directed to the problem. However, the application of transversely oriented elastic to the waist areas of a continuous assembly moving at high speed represents engineering difficulties of a much greater magnitude. This problem has not yet been solved to the satisfaction of most diaper manufacturers. Reference can be made to U.S. Pat. Nos. Joa, 4,284,454; Rega, 4,240,866 and Spencer, 4,523,969 as examples of machinery for applying transverse elastic. The Spencer patent describes apparatus having a plurality of heads moving orbitally along an elliptical path. These heads are designed to receive and hold two parallel strips of tensioned elastic. As the head is moving at its greatest velocity, at the end of its eliptical path, it contacts the transversely moving diaper assembly and transfers the elastic to the polyolefin backing film. A rotating mechanism attached to each head ensures that they remain oriented with their longitudinal axes always parallel as they travel around a central drive unit. The path of travel is controlled by a cam and follower mechanism which increases the radius of travel in the application zone.

The above-noted examples of machinery for applying transversely oriented elastic to a diaper assembly has been not entirely satisfactory for a number or reasons. In an effort to develop a superior system, the present inventor has searched other fields where a transversely moving first component is applied to a second component moving at right angles. In the field of bag making, U.S. Pat. Nos. 4,289,567 and 4,279,686 to Achelpohl might be noted. However, in this case the machinery operates in intermittent fashion with the second element being stopped during the period when the transversely moving first element is applied. This situation is similar to that shown by Wilson in U.S. Pat. Nos. 4,316,756 and 4,357,197 where pocket blanks are being applied in intermittent fashion to a moving garment portion. Urban et al, in U.S. Pat. No. 4,135,343 shows a similar intermittent operation where film is being enclosed within a paper mount to form photographic slides. Intermittent operation is also found in U.S. Pat. Nos. 2,601,005 to Rainey in apparatus to mount lead wires to a capacitor laminate and 3,960,641 to Pedersen where handle reinforcements are being placed on carrier bags. In the case of the latter inventor, opposed hexagonal rotary heads carry reinforcement labels which are applied to a moving strip of bag stock. At a second operation remote from this one, elongated hand holds are punched.

Truly continuous operation has been achieved in the diaper industry in the application of waistband adhesive attachment tapes. Examples of equipment to accomplish this function are shown in Wierzba et al, Nos., 3,728,191 and Babcock, 3,897,293. Endres, in U.S. Pat. No. 3,520,303, shows application of a barrier strip overlying the ends of an absorbent diaper pad. This represents a different and much simpler problem than that of applying a tensioned elastic article. In the latter case the elastic must generally be held in tension while it is bonded to the backing sheet or one of the other diaper components. This requirement greatly complicates the design of suitable machinery.

SUMMARY OF THE INVENTION

The present invention is an apparatus for applying tensioned elastic transversly of a moving web of material. The apparatus is suitable for application of the elastic at high line speeds without interuption or intermittent operation of the moving web. It is especially well adapted for the application of waist zone elastic to disposable diapers or similar products.

A first essential element of the apparatus is a support or frame which bears a shaft providing an axis of rotation for at least one rotatable radial arm. Normally the apparatus will have a plurality of equiangularly spaced radial arms proximally attached to a hub or similar structure rotatably journaled to the shaft. Each arm has a distally mounted rotatable polygonal head. The heads will be identical and each will have n peripheral edges which join to form a similar number of apices. Most typically n will be at least 3 and more usually 4. The heads have face portions oriented parallel to and are rotatable in a plane lying generally along a radius of the circle of rotation of the arm or arms and normal to the plane of the circle of rotation. Stated otherwise, the head may have two face portions which lie parallel to a longitudinal axis of the radial arm, said faces being perpendicular to the plane of the circle of rotation of the arm.

A drive is coupled to the arm assembly to rotate it about the shaft. There is also provided a head rotating means for moving each head $(360/n)°$ for each full rotation of the radial arm. Thus, if the head has four peripheral edges, it will rotate a one-fourth turn for each full rotation of the radial arm.

An elastic ribbon or ribbons pass through a feeder where they are tensioned and supplied to the periphery of the heads. Here clamps or a vacuum system retain them on the head periphery until such time as they are released to be applied to the moving web.

Finally, an anvil acts in opposition to the head at the time of application of the tensioned elastic ribbon to the moving web. In operation, the web is passed between the head and anvil along a path which describes a chord or tangent of the circle of rotation of the radial arm. In the preferred version of the invention the anvil has a plurality of faces and is rotated about an axis parallel to a radius of the circle of rotation of the radial arms. The anvil and radial arms are rotated respectively at peripheral speeds which are essentially equal to the linear speed of the web moving between them. This is critically important to the operation of the invention since it minimizes any shearing forces which would otherwise be placed on the moving web of material.

In the preferred version of the invention the apices of the polygonal head are truncated and the clamps or vacuum orifices to hold the tensioned elastic ribbons are located on these truncated portions. This way any clamps are located in a noninterfering position when the elastic ribbon is applied to the moving web. In the most usual procedure adhesive will be applied to the elastic ribbon before it is applied to the web. The opposite situation is equally acceptable where adhesive is applied to appropriate locations on the web prior to application of the elastic.

Most conveniently the head rotation system is a cam driven ratcheting device. This device can also be used to operate feed rolls which tension and advance the elastic ribbon.

It is an object of the present invention to provide apparatus for applying a tensioned elastic ribbon transverse to a moving web of material.

It is a further object to provide apparatus as described in which the web of material is moving at relatively high speed and in continuous or uninterrupted fashion.

It is another object to provide an apparatus for applying waist zone elastic to disposable diapers or similar products.

These and many other objects will become immediately apparent to those skilled in the art upon reading the following detailed description taken in conjunction with the drawings.

BRIEF DESCRIPTION OF THE DRAWINGS

FIG. 3 is a top plan view, partially cut away, of a single elastic applicator arm assembly.

FIG. 4 is a side elevation view of an elastic applicator head ratcheting and elastic advancing and severing mechanism.

FIG. 5 is a side elevation of an elastic applicator head ratcheting arm.

FIG. 6 is an elevation view of the leading side of an elastic applicator head.

FIG. 7 is an elevation view of the trailing side of an elastic applicator head showing the internal vacuum ducting and porting arrangement.

FIG. 8 is an elevation view of a vacuum control plate used in conjunction with an applicator head.

FIG. 9 is a detailed view of an elastic applicator head shaft.

FIG. 10 is an end elevation of an elastic applicator head showing the vacuum control plate assembly and a portion of the vacuum breaker mechanism.

FIG. 11 is an elevation view showing the linkage between the vacuum breaker mechanism and the elastic applicator head.

FIG. 12 is a detailed top plan view of the vacuum control cam follower and vacuum breaker control shaft.

FIG. 13 is a detailed description view of a portion of the vacuum breaker cam support arm taken along line 13—13 of FIG. 12.

FIG. 14 is a plan view of the main cam for controlling ratcheting of the elastic application head and of the vacuum breaker control cam.

FIGS. 15 and 16 are detailed side elevations of the vacuum breaker control cam taken respectively along lines 15—15 and 16—16 of FIG. 14.

DESCRIPTION OF THE PREFERRED EMBODIMENTS

Figure 1:
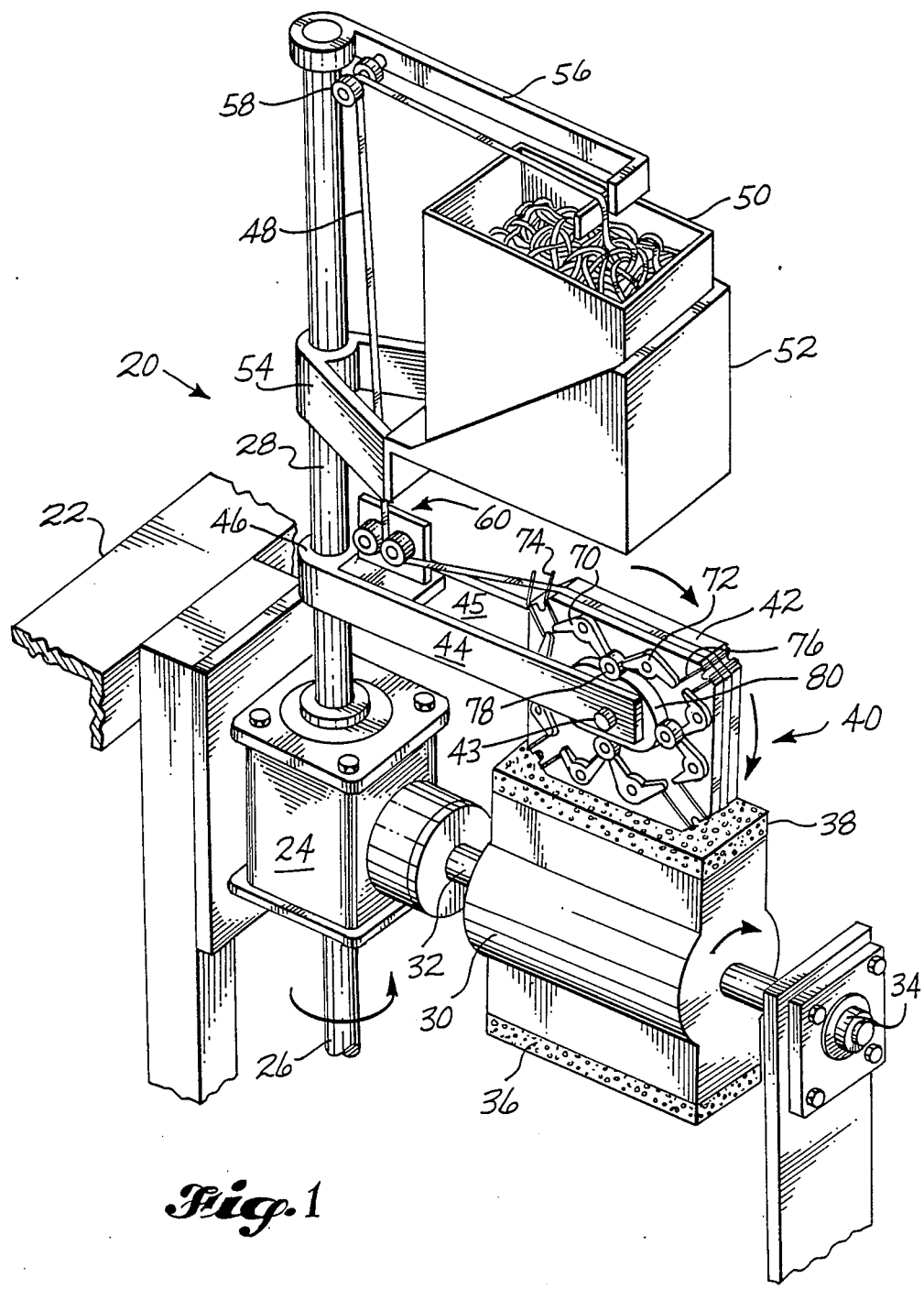
FIG. 1 is an overall perspective view of a transverse elastic applicator, shown for clarity as having only one radial operating arm.

The operation of the transverse elastic applicator can be best understood by reference to the drawings. FIG. 1 is an overall perspective view of one embodiment of the device. For ease in understanding the operation, the apparatus pictured in FIG. 1 has only a single operating arm and elastic applicator head. More typically there would be a plurality of identical arms, usually from four to six arranged in spider fashion from a common hub. The applicator is shown generally at 20. It has a main supporting frame 22 on which is mounted a transmission or gear box 24. A drive shaft 26 enters the transmission and is connected to a drive mechanism, not shown. A drive shaft 28 for the elastic applicator mechanism exits transmission 24. The shaft will normally be vertical and may or may not operate at the same speed as power input shaft 26. A rotating anvil 30 is attached to shaft 32 exiting the gear box at right angles to the drive/support shaft 28. The opposite or distal end of anvil drive shaft 32 is held in an outboard bearing 34 mounted on a member which is integral with frame 22. The rotating anvil has resilient surfaces 36,38 against which an elastic applicator head 40 can operate when applying transversly oriented elastic members to a continous moving web of material. This web may be a disposable diaper assembly or any similar product in which it is desirable to apply tensioned elastic in a direction which is transverse to the direction of movement of the material. The relationship between the moving web and the elastic applicator assembly is best seen by reference to FIG. 2 which will be described at a later time.

Elastic applicator head 40 is a subassembly which consists of the head member per se 42 mounted on an axle or shaft 43. The axle spans a pair of elongated support arms 44, 45 which are connected to a hub 46 affixed to shaft 28 so as to rotatable with it. An elastic ribbon or thread 48 is drawn from a supply container 50 cradled in an elastic container holder 52. This container holder is also connected to the drive/support shaft 48 by a hub member 54 so as to be rotatable with the shaft. Each operating arm and head assembly will have its own elastic ribbon supply. The ribbon is drawn from the supply box along a feed arm 56, over guide rolls 58, and through an elastic feed mechanism 60 which feeds a given length of elastic to the head each time it indexes. The amount of tension or stretch in the elastic applied to the web is controlled by the ratio of the length of one edge section of the applicator head divided by the length of untensioned elastic supplied by feed mechanism 60.

The elastic applicator heads are preferably polygonal when viewed in side elevation. Each head will have n peripheral edges, where n is at least 3 and preferably 4 to 6. In the present example the heads are shown as having 4 peripheral edges. Prior to the moment at which the elastic is actually applied to the moving web it will be present in tensioned form on three of the four edges. Some provision must be made for retaining the elastic so that the tensioning is not lost prior to application. A mechanical means of doing this is shown on head assembly 40 of FIG. 1. Here a set of pivotally attached arms 70, 72 bear elastic ribbon holding springs 74, 76. The position of these arms is controlled by a cam follower 78 acting against a cam 80 fixed to support arm 44. At the appropriate time the cam causes the retaining springs to open and release the tensioned elastic against the moving web held between head 42 and anvil surface 38. Normally adhesive will be applied to the elastic by conventional means, not shown, immediately prior to its application to the web. These adhesives are typically hot melt materials available from many suppliers and are commonly used in the manufacture of disposable diapers and related products.

Figure 2:
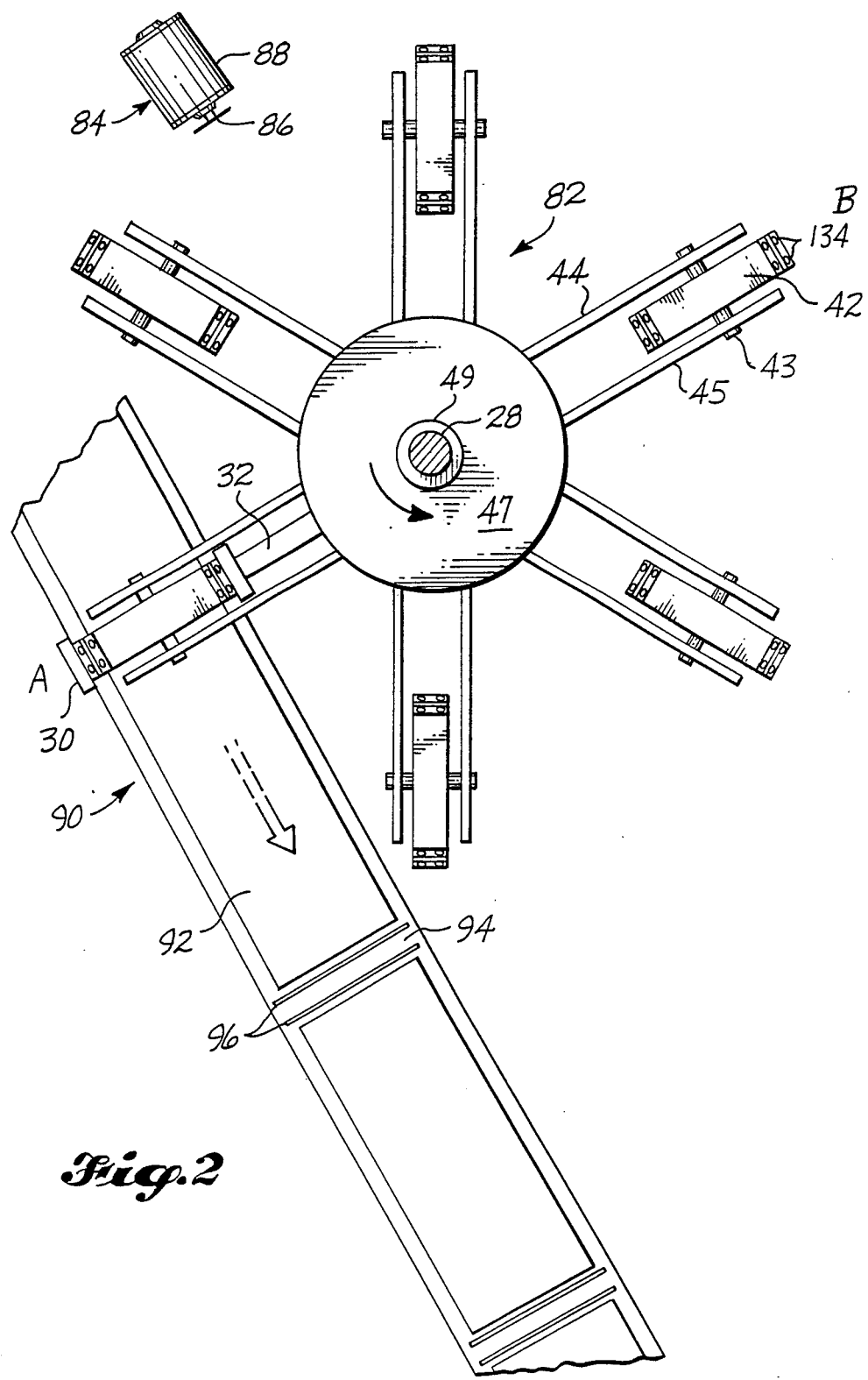
FIG. 2 is a simplified top plan view of the machine taken just above a complete arm assembly.

FIG. 2 is a top view of an elastic applicator having six identical arm and head assemblies. While a single such assembly, as is shown in FIG. 1, is fully operational, a multiple head assembly is desirable for use at the high line speeds experienced in a modern plant manufacturing disposable diapers. By using multiple arms the rotational speed of the head assemblies can be considerably lower and there is less possibility of introducing timing errors which could cause the elastic to be applied in the improper position. In the mechanism of FIG. 2 the arms are arranged spider fashion around a connecting plate 47 affixed to shaft 28 by hub 49. A ribbon severing device 84 separates the unit of elastic about to be applied from the continuous strand. This utilizes a rotary knife 86 driven by motor 88.

In the version of FIG. 2 and in all the subsequent figures, waistband elastic is being applied to a disposable diaper assembly. At each operation a strip of tensioned elastic is applied to the trailing end of one diaper and the leading end of the following diaper. An end-to-end diaper assembly 90 is shown having an absorbent pad area 92 and adjoining waistband zones 94. The applicator head assembly has applied tensioned elastic strips 96 in the waist zone. The elastic, not shown on the heads, is held on the heads by a series of vacuum orifices 134 and is applied to the diaper assembly when the vacuum is released on the lowermost peripheral face of the head.

The circumferential speed of the head assembly and the rotational speed of anvil 30 (FIG. 1) are timed to correspond to the linear speed of diaper assembly 90 so that a minimum of shearing stresses are encountered during the brief time interval when the stretched elastic is applied.

FIGS. 3-5 generally show the mechanism for ratcheting head 42 one-fourth turn for each full cycle of rotation of spider assembly 82. Head support arms 44, 45 are attached to a base plate 100, preferably by welding. This, in turn, is attached to the connecting plate 47 of the spider assembly by three machine screws 102, 104, 106. A linear bearing 108 is atached to base plate 100. Bearing rod 110 is supported at its distal end by the linear bearing. The proximal end of the bearing rod is clamped in cam follower bar 112 by a clamp screw 114. The opposite end of the cam follower bar bears a ratchet arm pin 116 pivotally mounted in ratchet arm 118. At right angles to the longitudinal axis of the cam follower bar is a rotatable cam follower 120 which operates against a main or head indexing cam 122. A ratchet arm bias spring 124 is attached at its proximal end to lug 125 on connecting plate 47. This spring maintains contact between cam follower 120 and main cam 122. Ratcheting pins 126, 128 are provided on one face of head 42. Also supported by arm 44 is a latch assembly 130 pivotally mounted to the arm at 132. This latch is held in place by a torsional biasing spring, not shown, and prevents any rearward rotation of the head which might otherwise be caused by the tensioned elastic. A latch stop pin 133 completes the assembly. Vacuum orifices 134 hold the tensioned elastic ribbon to the head as was previously described.

Each corner or apex of the head is truncated and this truncated portion contains the vacuum orifices 134 and a severing notch 140 which accommodates the rotating blade 88 of the elastic ribbn severing device 84. As shown in FIG. 4, elastic section 48' at the bottom of the head is now isolated from the rest of the elastic and ready for application.

The distal end 142 of ratchet arm 118 carries a notch which acts in conjunction with the four head ratcheting pins 126, 128 (only two of which are numbered) to advance the head one-fourth turn for each full revolution of spider assembly 82. This will normally occur as the head rotates between positions A and B as shown on FIG. 2.

Referring again to FIG. 4, elastic ribbon 48 is drawn from supply 50 and at the location of the application arm passes over a reversing roll 146 and then between pinch roll 148 and drive or feed roll 150. The drive roll is mounted on a pair of stubby supports 152 welded to support arms 44, 45. The drive roll 150 is affixed to a shaft 154 rotably journaled in support arms 152. Affixed to the shaft is a pendant tape tension adjustment arm 156. A linking member 158 is pivotally attached to the tape tension adjustment arm at 160. The opposite end of the linking member 158 is pivotally attached at 162 near the distal end of the ratcheting arm. Tension adjustment arm 156 is normally slotted so that the connection 160 may be moved closed to or further from central axis 154 in order to control the amount of elastic ribbon fed to the head assembly. This, in turn, controls the amount of stretch in the elastic. Drive roll 150 is equipped with an internal ratchet or overrunning clutch, not shown, so that the rim does not move backwards when linking member 158 retracts to being a new stroke.

FIG. 5 presents a more detailed view of ratcheting arm 118.

FIGS. 6-10 show more detailed views of the elastic applicator head. FIG. 6 shows the leading side or face where ratcheting pins 126, 128, only two of which are numbered, are held in place by lock nuts 127, 129. The head has a central aperture 170 where it can be rotatably mounted on a fixed shaft 190. Grooves 140, cut into the truncated corner sections, accommodate the rotating blade 86 of the elastic severing assembly 84.

The opposite or trailing face of the head is shown in FIG. 7. This face has a control plate engaging surface 172 and external vacuum ports 174, 174' which are in communication with the internal ducting 176 leading the external vacuum orifices 134 which hold the elastic ribbon in place. As is seen in FIG. 10, both side-by-side vacuum orifices 134 are connected to a common external orifice 174. Orifices 134' are similarly connected to a common orifice 174' on the control plate engaging surface. The control plate 178, shown in FIG. 8, is a part of the mechanism for holding the elastic to the head and then releasing it at the time of application. Control plate 178 has a groove 180 machined into the face which contacts the engaging surface 172 on the trailing face of the head. Groove 180 covers approximately 150° of angle and at one end is in communication with a vacuum line connection 182. A vacuum release port 184 is drilled through the face of the plate. Whether a section of elastic on the head is held or released by vacuum ports 134 is determined by the position of head 178 relative to applicator head 42. When groove 180 in the control plate is opposite external ports 174 of the taper head, the elastic ribbon will be held by the vacuum. However, when control plate 178 is rotated slightly so that aperture 184 is opposite external port 174 on the applicator head, the vacuum will be released and the elastic ribbon can be applied to the moving diaper assembly. Rotation of the plate is caused in part through the action of position control arm 186 and linking arm 187 which are pivotally connected to the control plate 188.

Referring now specifically to FIGS. 9-12, the action of the vacuum control assembly will be further explained. FIG. 9 is a detailed view of shaft 43 which mounts the applicator head 42 to arms 44, 45. This has a main portion 190 on which head 42 rotates and a somewhat enlarged section 192 on which vacuum breaker plate 178 is mounted. It should be noted that the vacuum breaker plate remains in essentially fixed position as the head is indexed or ratcheted forward. Shaft 43 further has drilled and taped end portions 194, 196 for retainer bolts 195, 197 (FIG. 10).

FIG. 10 is an end elevation of the ribbon applicator head 42 shown mounted between support arms 44, 45. This view is particularly intended to show, in part, the operation of the vacuum breaker mechanism. Here vacuum control plate 178 is seen in position against the trailing side of head 42. A vacuum control plate actuating shaft 200 is journaled in a distal end retaining block 202 held to support arm 45 by bolts 204, 206. A distal end shaft clamp 208 bears a rigidly attached linking arm 210. The opposite end of this arm is pivotally joined to linking arm 187 of vacuum control plate position control arm 186 where it is held by a retaining nut 189. When the control plate actuating shaft 200 is rotated clockwise, as seen in FIG. 10, the control plate of FIG. 8 will be rotated in a counter-clockwise direction. Conversely, when shaft 200 is rotated in a counter-clockwise direction, control plate 178 will be rotated clockwise so that vacuum release orifice 184 overlies one of the external ports 174 in the applicator head.

FIG. 11 is an expanded view of the vacuum control assembly. The proximal end of control shaft 200, opposite from the end attached to vacuum control plate 178, is journaled in a proximal end bearing block 212. This is attached to support arm 45 by bolts 214, 215. A cam follower support arm 216 is clamped by bolt 217 to the extreme proximal end of control shaft 200 (FIGS. 12 and 13). The other end of cam follower support arm 216 bears cam follower 218 which is rotatably mounted on a bolt 220 retained by nut 222. A torsional biasing spring 224 has one end anchored in a spring retainer 226, mounted on control rod 220, and the other end is anchored in proximal end bearing block 212. This provides biasing to the vacuum control system so that cam follower 218 is in proper position to engage its actuating cam 230, shown in FIGS. 14-16. This cam has an incoming end 234 which lifts it to rotate shaft 200 an appropriate amount, to cause release of the vacuum, and then drops it into its resting position as it leaves the cam by ramp 236.

The overall operation of the elastic applicator will now be briefly described. The elastic ribbon drawn from reservoir 50 is held on three edges of applicator head 42. A diaper assembly 90 passes between applicator head 42 and rotating anvil 48. At the proper time vacuum control cam 230 releases parallel sections of elastic ribbon against the diaper assembly. However, the vacuum is maintained on the other two faces of the applicator head where elastic ribbon is present. Immediately after applying the ribbon to the diaper, the assembly has rotated past the application station. The head indexing mechanism then comes into play and ratchets the head one-fourth turn in clockwise manner to add tensioned elastic ribbon to another edge of the applicator head. This operation is again repeated when the spider bearing the heads has made a full revolution.

It will be understood by those skilled in the art that many variations would be possible in the present invention. It is the intent of the inventor that these variations be included within the scope of the invention insofar as they are found within the appended claims.

I claim:

1. Apparatus for transversely applying a tensioned elastic ribbon to a moving web of material which comprises:
   a supporting frame bearing a shaft providing an axis of rotation;
   at least one rotatable radial arm means journaled proximally to said shaft, the arm means having a distally mounted rotatable polygonal head means, said head means having n peripheral edges joining to form n apices, where n is at least 3, said head means having face portions oriented parallel to and being rotatable in a plane lying generally along a radius of the circle of rotation of the arm means and normal to the plane of said circle of rotation;
   drive means for rotating the arm means;
   rotating means for moving the head means (360/n)° for each full rotation of the radial arm means;
   feed means for tensioning and supplying at least one strand of elastic ribbon to the periphery of the head means;
   holding means for retaining the tensioned elastic ribbon on the periphery of the head means and subsequently releasing it from the head means in order to apply it to a moving web; and
   anvil means acting against the head means at the time of application of said tensioned elastic ribbon to the moving web, when said web is passed between the head means and anvil means along a path describing a chord or tangent of the circle of rotation of the radial arm means.

2. The apparatus of claim 1 which includes a plurality of equiangularly spaced radial arm means.

3. The apparatus of claim 1 including means to rotate the anvil about an axis parallel to a radius of the circle of rotation of the radial arm means, wherein said anvil and arm means may each be rotated at a peripheral speed essentially equal to the linear speed of the moving web means.

4. The apparatus of claim 3 in which the anvil has a plurality of faces which sequentially oppose a head means at the time of application of the elastic ribbon to the moving web.

5. The apparatus of claim 1 in which the holding means on the head means for the tensioned elastic ribbon comprises mechanical clamps mounted adjacent each apex of the polygonal head means.

6. The apparatus of claim 1 in which the holding means on the head means for the tensioned elastic ribbon comprises orifices in communication with a vacuum system, said orifices being located adjacent each apex of the polygonal head means.

7. The apparatus of claim 5 in which the apices of the polygonal head means are truncated and the clamps are mounted on the truncated portion so as to be in a noninterfering location when the elastic ribbon is applied to the moving web.

8. The apparatus of claim 6 in which the apices of the polygonal head are truncated and the vacuum orifices are located on the truncated portions.

9. The apparatus of claim 1 which further includes severing means associated with the head means for severing individual elastic units from the elastic ribbon prior to application to the moving web.

10. The apparatus of claim 1 in which the head rotation means comprises a ratcheting means.

11. The apparatus of claim 10 in which the ratcheting means also drives the elastic feed means for advancing the elastic ribbon.

12. The apparatus of claim 10 in which the ratcheting means is driven by a cam means.

13. The apparatus of claim 11 in which the ratcheting means is driven by a cam means.

14. The apparatus of claim 6 which further includes vacuum breaking means for releasing the elastic ribbon from the head means at the time of application to the moving web.

15. The apparatus of claim 8 which further includes vacuum breaking means for releasing the elastic ribbon from the head means at the time of application to the moving web.

* * * * *